United States Patent
Grob et al.

(10) Patent No.: US 6,257,047 B1
(45) Date of Patent: Jul. 10, 2001

(54) METHOD AND APPARATUS FOR THE INTRODUCTION OF LARGE VOLUME SAMPLES IN CAPILLARY COLUMNS FOR GAS CHROMATOGRAPHY

(75) Inventors: Konrad Grob, Fehraltorf (CH); Fausto Munari, Milan (IT); Pier Albino Colombo, Treviglio; Paolo Magni, Besana Brianza, both of (IT)

(73) Assignee: Themoquest Italia S.p.A., Rodano (IT)

( * ) Notice: Subject to any disclaimer, the term of this patent is extended or adjusted under 35 U.S.C. 154(b) by 0 days.

(21) Appl. No.: 09/315,697

(22) Filed: May 20, 1999

(30) Foreign Application Priority Data

May 22, 1998 (IT) .............................. MI98A1142

(51) Int. Cl.[7] .......................... B01D 15/08; G01N 30/04; F16K 31/02
(52) U.S. Cl. ..................... 73/23.42; 73/23.22; 73/23.41; 422/89; 95/87; 95/89; 96/105
(58) Field of Search .................. 73/23.42, 23.41, 73/23.22, 23.35; 422/70, 89; 95/87, 89; 96/105

(56) References Cited

U.S. PATENT DOCUMENTS

| | | | | |
|---|---|---|---|---|
| 3,444,722 | * | 5/1969 | Roof | 73/23.1 |
| 4,373,549 | * | 2/1983 | Nalepa | 137/487.5 |
| 4,422,860 | * | 12/1983 | Feinstein | 55/67 |
| 4,980,131 | * | 12/1990 | Meuzelaar et al. | 422/78 |
| 5,339,673 | * | 8/1994 | Nakagawa et al. | 73/23.36 |
| 5,379,629 | * | 1/1995 | Mueller | 73/23.27 |
| 5,467,635 | * | 11/1995 | Nakagawa et al. | 73/23.35 |
| 5,672,810 | * | 9/1997 | Shibamoto | 73/23.25 |
| 5,779,765 | * | 7/1998 | Grob et al. | 95/83 |
| 5,827,945 | * | 10/1998 | Arnold | 73/23.42 |
| 6,062,065 | * | 5/2000 | Sugimoto et al. | 73/23.42 |

* cited by examiner

*Primary Examiner*—Hezron Williams
*Assistant Examiner*—David J. Wiggins
(74) *Attorney, Agent, or Firm*—Cobrin & Gittes

(57) ABSTRACT

The invention concerns a method and an apparatus for the direct injection of large volumes (>3 $\mu$l) of samples into the column in a gas chromatography analysis apparatus comprising an oven, a gas chromatography column lodged in the oven, a means for the direct transfer into the column of the sample and a source of carrier gas upstream the column, as well as a detector downstream the column.

According to the invention two or more of the parameters:
- nature of the solvent
- injection rate
- flow-rate and/or pressure of the carrier gas
- temperature at least of an initial length of the column during the injection are correlated and/or controlled to achieve a control of the length of the zone wetted by the sample during its introduction.

26 Claims, No Drawings

METHOD AND APPARATUS FOR THE INTRODUCTION OF LARGE VOLUME SAMPLES IN CAPILLARY COLUMNS FOR GAS CHROMATOGRAPHY

BACKGROUND OF THE INVENTION

1. Field of the Invention

The present invention operates in the field of gas chromatography with capillary columns and more particularly refers to the introduction of large volume liquid samples directly into a capillary column (on-column injection) for subsequent analysis of the same in a known gas chromatography apparatus.

The introduction of large volume liquid samples (samples are formed by the substances to be analyzed strongly diluted in a proper solvent) allows analysis of compounds at very low concentrations or with very small quantity of substance, since the whole sample can be injected, even if problems can arise due to the large quantity of solvent introduced.

"Large volume" as here used means a quantity of sample which is relatively large compared to the volume conventionally injected with splitless or on-column modes. A precise definition of large volume doesn't exist, but generally, the introduction of a sample larger than 3 $\mu$l in columns of small inside diameter (0,2 mm or less) and larger than 5 $\mu$l in columns of bigger diameter is considered "large volume".

Large volumes of sample are introduced following the known on-column technique or vapor splitting technique named Programmed Vaporizing Temperatures (PTV) in the "solvent splitting" mode.

The present invention relates to the on-column technique.

2. Description of the Prior Art

To accelerate the unloading of the solvent vapors, a solvent vapor exit duct is placed in derivation on a gas chromatography column-pre-column connection.

This duct is kept open for the time necessary to eliminate most of the solvent vapors and then is closed to send the remaining part of solvent and the substance to be analyzed into the gas chromatography column, according to a well known methodology.

The main problem of these techniques arises from the need to unload the solvent vapors in such a way that the components of the substance remain at the entry of the column.

To solve this problem two different methodologies have been developed that are distinguished by their behavior towards the volatile element and are called respectively:

Concurrent solvent evaporation, and

Partially concurrent solvent evaporation, which is achieved with the help of a pre-column and the re-concentration of the sample by means of the "retention gap" technique.

The first methodology (concurrent evaporation) provides for the introduction of the sample directly into a pre-column using such injection conditions to obtain that all the solvent evaporates during its introduction; in particular, the injection rate of the solvent into the pre-column must be equal or less than the vaporization rate of the solvent in the pre-column.

This concurrent solvent evaporation technique provokes losses of components of the sample that are eluted at oven temperatures under around 120–150° C. (if injected in volumes greater than 100 $\mu$l and dissolved in a volatile organic solvent). Its field of application is therefore narrow.

On the other hand, the definition of operational conditions is simpler, the pre-columns could be short (typically 1–2 m) and virtually limitless volumes of sample could be injected. For this reason, it is the preferred technique for in line LC—GC (liquid chromatography—gas chromatography) when the components to be analyzed permit its use.

Therefore, concurrent solvent evaporation is used mainly in LC—GC chromatography joined in line, where the LC fractions, normally of 200–1000 $\mu$l, are introduced in GC. According to the state of the art, the introduction is mainly effected by means of a loop type interface. The plug of liquid sample is made to advance by the carrier from a loop of sample within an uncoated (no stationary phase) pre-column of 1–3 m.

The temperature of the pre-column, or more exactly of the oven in which the pre-column is lodged, is selected so that the vapor pressure of the solvent at the front end of the liquid sample stops the flow and prevents it from penetrating in depth into the column.

The advantage of the introduction through the loop is that the introduction rate is self regulated. The disadvantage, however, is often of a violent movement of the liquid forward and back for a distance that easily extends for 1,5 m. The components of the sample are then deposited along all the length of the wet zone.

As an alternative, the concurrent solvent evaporation is achieved by means of introduction of the sample at a controlled rate. The carrier is switched-off and a pump pushes the liquid sample to the entry of the column in the GC oven. The oven temperature is selected in such a way as to be sufficiently elevated to create a solvent vapor pressure that unloads the vapors of solvent from the introduced liquid. Both the techniques are called "vapor overflow" because there is no flow of carrier gas during the introduction of the sample.

The methodology called "partially concurrent solvent" evaporation (with retention gap) provides that the flow of carrier gas is active during the introduction and that the evaporation rate is lower than the injection rate, so that at least part of the sample is distributed as a liquid in the entry of the column, forming an expanding wet zone. The entry of the column consists usually of a relatively large uncoated pre-column.

The liquid sample at the entry of the column is used to trap the volatile components of the sample in the solvent (solvent trapping). This allows the solvent to vaporize and unload without loosing the solutes. The solutes are re-concentrated at the entry of the analytical column and the chromatographic process begins. Solvent trapping uses the liquid sample as a temporary gas-chromatographic stationary phase to hold back the volatile components of the sample. Since the sample film has a thickness of the order of 10–30 $\mu$m, its retention power is high. To be effective, the liquid sample layer must be downstream of the evaporation point, so that the components contained in the unloaded solvent vapors can be extracted and held back. The solvent trapping has been described in K. Grob, in: "On-Column injection in Capillary GC," Huethig, Heidelberg, 1987, 1991.

Because of the entrapment by the solvent, the technique of partially concurrent solvent evaporation (retention gap) has a much wider field of application than the technique of concurrent evaporation: virtually all the components of the sample eluted after the solvent can be analyzed quantitatively. Since the zone wetted by the sample is long, it is necessary to use an uncoated pre-column to tighten the initial bands of the retention gap effect. It must be relatively long (typically 10 m×0.53 mm i.d.), and this could constitute a drawback for the analysis of given types of components.

According to the conventional theory, the liquid sample is injected at a rate greater than the vaporization rate, so that the liquid sample undergoes to an expansion in the column (retention gap with solvent trapping technique), or the sample injected at a lower rate so that a concurrent evaporation without solvent trapping is obtained. Therefore, always according to the traditional technique, the solvent trapping seems to be tied to the liquid that expands in a pre-column.

OBJECTS OF THE INVENTION

On that premise, an object of the present invention is to eliminate the aforementioned and other drawbacks of the known methodologies as illustrated above, by carrying out a direct introduction (on-column) of large volumes of sample in an entry section of the column sufficiently short to prevent a widening of the peaks due to excessively long initial bands, by carrying-out a direct introduction (on-column) of large volumes of sample in a section of column or in a pre-column having a length of 0,5–2 m that can be coated with stationary phase if required, to take advantage of an higher inertia, and by achieving a high retention power of the volatile components of the sample by means of the formation of a layer of liquid sample having a limited length.

According to the invention, the foregoing is achieved by carrying-out a method of injection as defined in claim 1.

In an actual embodiment, the method according to claim 7 is particularly suggested.

The apparatus for carrying-out the method according to the invention will be configured as in claim 14 and following Claims.

DESCRIPTION OR PREFERRED EMBODIMENTS

In practice, by the method of the invention a sort of concurrent solvent evaporation is obtained, where, however, the introduction of the sample happens with a current of carrier gas.

The direct introduction of the sample to the entry of a coated or uncoated column or pre-column is possible because the zone wetted by the sample is so short that the resulting initial bands of solutes are sufficiently short to prevent a widening of the peaks.

The short initial band is obtained by means of releasing the liquid sample at a carefully controlled rate at the entrance, for instance by means of an auto-sampler with carefully controlled injection rate, or with a suitable device applied to a direct on-column injector, or again by means of a LC-GC transfer device.

To achieve a concurrent solvent evaporation with an injectiong system and a unloading of the carrier gas according to the invention, the temperature of the column must be at least 1–20° C. above the dew-point of the solvent vapor/carrier gas mixture at the entry pressure. Below the dew-point, the vaporization is not fully concurrent and the wet zone expands in the entry of the column or pre-column.

The proposed technique produces a wetted zone at the entry of the column or pre-column that has a constant length after a brief initial time period to reach a stable condition. It could be kept sufficiently short to allow direct introduction of the sample onto a coated column. The technique uses an initial length or entry section that is at a temperature slightly lower than or equal to the dew-point of the solvent vapor/carrier gas mixture, while the remaining length of the column or pre-column is above this temperature.

The preferred method of lowering the temperature in said entry section to or below the dew point exploits the cooling effect of the solvent vaporization. If the initial length of the column or pre-column is subject to the over inner temperature, this temperature is maintained above the dew-point for such a value that the heat subtraction due to the solvent evaporation cools an initial length of the column or pre-column suitable for the application.

The liquid sample initially introduced is transferred to the wall of the capillary column which is at a temperature above the dew-point of the solvent vapor/carrier gas mixture and is completely vaporized. A small quantity of evaporated solvent is sufficient to cool the vaporization zone to a temperature slightly below the dew point. Accordingly, part of the following liquid will flow more deeply into the column or pre-column, where the process is repeated. The wet zone expands until reaching such a length to give rise to the required capillary surface area to enable a heat transfer for the vaporation of the solvent from the atmosphere surrounding the zone of vaporization.

This initial period, which is necessary to reach a stable condition, can be shortened by injecting a first part of the sample at a faster rate, so that a negligible quantity of the sample is vaporized before getting the entrapment effect by the solvent. Another possibility foresees an initial injection of pure solvent.

It should be noted that the temperature control of the column or pre-column doesn't require of be effected with extreme precision, since, all other factors being equal, the wet zone will be consequently extended or shortened.

The technique preferably involves an exit of vapor. After a pre-column of, for instance, 1–2 m×0.53 mm i.d., a T-piece is installed to carry the vapor to the separation column and to an exit. This exit is opened during the vaporization of the solvent and is normally closed at the end of the introduction of the sample.

The method can foresee an initial length of column or pre-column at least partially separated from the oven atmosphere by means of a tube which can be in case isolated and/or thermostat controlled. This tube can be similar to a known device used for the on-column injection at elevated oven temperature. In this way, the cooling of the evaporation zone is more pronounced so that the choice of oven temperatures is less critical. If the initial length of column or pre-column is actively cooled during the injection and the solvent evaporation period, the injection can be carried-out with higher oven temperatures, thus accelerating the analysis by avoiding the cooling of all the oven for the injection.

This tube can be actively heated to a temperature higher than that of the oven after the solvent vaporization period, to shorten the initial solute bands and overcome the retention power of other materials of the sample (such as non-evaporating by-products, for instance).

The application of the proposed technique involves the determination of the dew point of the solvent vapor/carrier gas mixture, in order to set the injection conditions. This value could be obtained by means of an approximate calculation, considering a static condition of the stationary state in the wet zone of the column or pre-column and hypothesizing a constant composition of the of solvent vapor/carrier gas mixture.

In practice, the molar flow rate of the carrier is obtained from the knowledge of the mass flow rate of same, $$F_{n\ carrier} = \frac{F_{m\ carrier}}{M_{carrier}}$$

where $F_{n\ carrier}$: molar flow rate of the carrier;
$F_{m\ carrier}$: mass flow rate of the carrier;
$M_{carrier}$: molecular weight of the carrier;

Similarly, it is possible to obtain the molar flow rate of the solvent vapor:

$$F_{n\ solv} = \frac{\mu_{in}\rho}{M_{solv}}$$

where $F_{n\ solv}$: molar flow rate of the solvent
$\mu_{in}$: injection rate
$\rho$: density of the liquid solvent
$M_{solv}$: molecular mass of the solvent The molar fraction of the of solvent vapor $X_{solv}$ is then given by:

$$X_{solv} = \frac{F_{n\ solv}}{F_{n\ solv} + F_{n\ carrier}}$$

and the partial pressure of the solvent $p_{vap}$ is obtained from the total pressure $p_{tot}$ as follows:

$p_{vap} = p_{tot} X_{solv}$

From the formula of Antoine:

$$\ln p_{vap} = A \frac{B}{T_{dew} + C}$$

in which A, B and C are constants that depend on the nature of the solvent, the dew point temperature $T_{dew}$ of the mixture can be calculated.

The sample introduction conditions can be set by means of a thermocouple fixed to the external wall of the column. The thermocouple is installed at a point that is considered to be the frontal end of the maximum tolerable length of the wet zone and detects the cooling derived from the solvent vaporization inside the capillary, if the liquid reaches this point.

What is claimed is:

1. A method for performing a direct on-column injection of large volumes (>3 µl) of samples (comprising the substance to be analyzed and a solvent) in an gas chromatography analysis apparatus comprising an oven, a gas chromatography column lodged in the oven, a means for the direct transfer into the column of the sample along a column zone during a sample introduction time and a source of carrier gas upstream the column, as well as a detector downstream the column, characterized by the correlation and control of two or more of the following parameters used to define a known set of injection conditions:

nature of the solvent and a solvent vapor resulting therefrom
rate of sample and solvent injection
flow-rate and/or pressure of the carrier gas
temperature, over at least of an initial length of the column during the injection, where said method also comprises an injection means to control the length of the column zone wetted by the sample during its introduction, along at least part of said initial column length.

2. A method according to claim 1, characterized by correlation and control of said parameters to obtain a presence, during the injection, of a wet stable column zone less than about 50 cm in length, along said initial column length.

3. A method according to claim 1, characterized in that a initial column length is formed by or belongs to a pre-column, and in that a unloading of solvent vapors is provided for between said pre-column and column, substantially during the injection.

4. A method according to claims 1, characterized in that the temperature of said initial column or pre-column length is controlled by controlling the temperature of a environment surrounding the said initial length.

5. A method for promotion an evaporation of said solvent according to claim 4, characterized by an increase of the temperature of said environment surrounding the initial column or pre-column length at an end of the solvent evaporation.

6. A method according to claim 1, characterized by the steps of:

ascertaining the nature of the solvent;
establishing an injection rate value;
establishing a value of flow-rate and/or pressure of the carrier gas;
calculating a dew-point of the solvent/carrier gas mixture inside the initial column or pre-column length in the injection conditions;
imposing a temperature value above said dew-point for a preset amount of the environment surrounding said column or pre-column during the injection.

7. A method according to claim 6, characterized in that, in presence of volatile components the sample, the temperature of the environment surrounding the column or pre-column initial length is above said calculated dew point for an amount between 1 and 20° C.

8. A method according to claim 3, characterized by the introduction of the sample into a pre-column not coated with a stationary phase.

9. A method according to claim 3, characterized by the introduction of the sample into a pre-column coated with a stationary phase.

10. A method according to claim 1, characterized by the final introduction of a first sample portion at a more elevated rate compared with the introduction rate of a remaining sample portion that remains over after the initial introduction of said first sample portion.

11. A method according to claim 1, characterized by the introduction of a pure solvent concentration immediately before the introduction of the sample.

12. A method according to claim 1, characterized by detection of the temperature in an end point on the outside of said column or pre-column initial length and by control of the sample introduction rate on the basis of said temperature detection.

13. A gas chromatography analysis for implementing direct on-column injection of large volumes (greater than 3 microliters) of samples (comprising the substance to be analyzed and a solvent) apparatus comprising an oven, a gas chromatography column lodged in the oven, a means for introducing direct transfer into the column of the sample and a source of carrier gas upstream the column, as well as a detector downstream the column, characterized in that said detector comprises means for controlling the temperature of an environment surrounding an initial column length of a column zone wetted by the sample during its introduction therein, as well as means for controlling the sample injection rate and solvent injection rate.

14. An apparatus according to claim 13, further comprising means for determination and control of a flow-rate and/or pressure of the carrier gas.

15. An apparatus according to claim 13, characterized in that said means for controlling the sample injection rate are pre-set to operate at rates between 0.03 and 20 $\mu$l/sec.

16. An apparatus according to claim 15, characterized in that said means for controlling the sample injection rate carry-out the injection at a constant and predetermined rate.

17. An apparatus according to claim 16, characterized in that said means for controlling the sample injection rate carry-out the injection at at least two different rates.

18. An apparatus according to claim 13, characterized in that said means for the direct transfer into the column of the sample comprises an on-column direct injector.

19. An apparatus according to claim 13, characterized in that said means for the direct transfer into the column of the sample comprises an automatic sampler.

20. An apparatus according to claim 13, characterized in that said means for the direct transfer into the column of the sample comprises a LC—GC transfer device.

21. An apparatus according to claim 16, characterized in that said column initial length is formed by or belongs to a pre-column, and in that said column initial length comprises a deviation between an analytical column and the pre-column, said column initial length also being equipped with valve means for the control of the solvent vapors unloading substantially during the sample injection.

22. An apparatus according to claim 21, characterized in that said pre-column is not coated with stationary phase.

23. An apparatus according to claim 21, characterized in that said pre-column is coated with a stationary phase.

24. An apparatus according to claim 13, characterized in that the environment surrounding said column or pre-column initial length is constituted by an inside of said gas chromatography oven.

25. An apparatus according to claim 13, characterized in that said environment surrounding the column or pre-column initial length is constituted by an inside of a tube surrounding said initial length and having a thermally controlled atmosphere.

26. An apparatus according to claim 13, characterized in that a temperature detecting means is fitted on an outside of said column or pre-column initial length, in proximity of a length downstream end.

* * * * *